United States Patent [19]

O'Reilly et al.

[11] Patent Number: 5,389,370

[45] Date of Patent: Feb. 14, 1995

[54] ACTIVE COMPONENT CONCENTRATES AND NEW ACTIVE COMPONENT COMBINATIONS FROM GINKGO BILOBA LEAVES, THEIR METHOD OF PREPARATION AND PHARMACEUTICALS CONTAINING THE ACTIVE COMPONENT CONCENTRATES OR THE ACTIVE COMPONENT COMBINATIONS

[75] Inventors: Joseph O'Reilly, Glounthaune, Ireland; Hermann Jaggy, Bad Schönborn, Germany

[73] Assignee: Montana Limited, Little Island, Ireland

[21] Appl. No.: 909,137

[22] Filed: Jul. 6, 1992

Related U.S. Application Data

[63] Continuation of Ser. No. 623,861, Dec. 4, 1990, abandoned.

[30] Foreign Application Priority Data

Dec. 4, 1989 [DE] Germany ............................ 3940094

[51] Int. Cl.⁶ .................... A61K 35/78; A61K 31/70
[52] U.S. Cl. .................................... 424/195.1; 514/27
[58] Field of Search ........................ 424/195.1; 514/27

[56] References Cited

U.S. PATENT DOCUMENTS

| | | | |
|---|---|---|---|
| 4,708,949 | 11/1987 | Liu | 514/26 |
| 4,753,929 | 6/1988 | Matsumoto | 514/27 |
| 4,886,904 | 12/1989 | Tanaka | 560/249 |
| 4,892,883 | 1/1990 | Chatterjee | 514/464 |
| 4,981,688 | 1/1991 | Ayroles | 424/195.1 |

FOREIGN PATENT DOCUMENTS 0324197 7/1989 European Pat. Off. .

OTHER PUBLICATIONS

Nakanishi, K., et al. *The Gingkolides* pp. 89–113 (1967).
Maruyama, M., et al. "The Ginkgolides I. Isolation and Characterization of the Various Groups" Tetra. Lett. No. 4, pp.299–302 (1967).
Okabe, K., et al. "Gingkolides" J. Chem. Soc. pp. 2201–2206 (1967).
Nakanishi, K., et al., *J. Am. Chem. Soc.* 93:3544–3547 (1971).
Gellerman, J. L., et al. *J. Anal. Chem.* 40:4:739–743 (1968).
Gellerman, J. L. *Phytochem.* 15:1959–1961 (1976).
Hill, G. A. et al. *J. Am. Chem. Soc.* 56:2736–2738 (1934).
Sowers, W. F. et al., *Arch. Derm.* 91:452–456 (1965).
Nakamura, T. *Contact Derm.* 12:281–282 (No. 5, 1985).
Becker, L. E. et al. *J. Am. Med. Assoc.* 231:1162–1163 (No. 11, 1975).

*Primary Examiner*—William H. Beisner
*Assistant Examiner*—Ralph Gitomer
*Attorney, Agent, or Firm*—Kenyon & Kenyon

[57] ABSTRACT

The invention relates to highly concentrated active component concentrates and new active component combinations from *Ginkgo biloba* leaves as well as their method of preparation and the pharmaceuticals containing these active component concentrates or active component combinations.

20 Claims, No Drawings

ACTIVE COMPONENT CONCENTRATES AND NEW ACTIVE COMPONENT COMBINATIONS FROM GINKGO BILOBA LEAVES, THEIR METHOD OF PREPARATION AND PHARMACEUTICALS CONTAINING THE ACTIVE COMPONENT CONCENTRATES OR THE ACTIVE COMPONENT COMBINATIONS

This application is a continuation of application Ser. No. 07/623,861, filed on Dec. 4, 1990, now abandoned.

The invention relates to highly concentrated active component concentrates and new active component combinations from *Ginkgo biloba* leaves as well as their method of preparation and the pharmaceuticals containing these active component concentrates or active component combinations.

Extracts from the leaves of *Ginkgo biloba* have been used for a long time for the therapy of peripheral and cerebral arterial circulatory disturbances. Methods of preparation of *Ginkgo biloba* extracts with a greatly enriched content of flavone glycosides as the active components are known; see DE-B 17 67 098 and DE-B 21 17 429. These extracts are also referred to as *Ginkgo biloba* monoextracts.

EP-A 0 324 197 describes a method of preparation of an extract from *Ginkgo biloba* leaves in which an aqueous solution of a lower alcohol or ketone, obtained after extraction of the leaves, is concentrated in the presence of kieselguhr. The resultant aqueous suspension is filtered through kieselguhr, the fitrate is extracted with butanone and the extract is freed from the solvent.

EP-A 330 567 relates to a method of preparation of an extract from *Ginkgo biloba* leaves in which the crushed leaves are extracted with an aqueous ketone compound. This extract is concentrated until biflavones and hydrophobic compounds precipitate. After filtration the aqueous concentrate is rendered alkaline, whereby the proanthocyanidins precipitate.

After separation of the precipitate and acidification of the filtrate, a liquid-liquid-extraction is carried out with a $C_{4-6}$-ketone compound in the presence of ammonium sulfate. The extract is obtained after stripping of the ketone compound.

DE-A 35 14 054 has disclosed that the ginkgolides, known components of the *Ginkgo biloba* leaves which are terpenoid substances with lactone structure (see K. Nakanishi, Pure and Applied Chemistry, Vol. 14 (1967), 89–113, and M. Maruyama et al., Tetrahedron Letters (1967), 299–302 and 303–319, and K. Okabe et al., J. Chem. Soc. (1967), 2201–2206), can be used to treat illnesses and similar conditions caused by PAF ("Platelet Activating Factor").

The use of bilobalide, a sesquiterpene lactone structurally related to ginkgolides (K. Nakanishi et al., R. T. Major et al., and K. Weinges et al., J. Am. Chem. Soc., Vol. 93 (1971), 3544–3546) is known from DE-A 33 38 995 and the corresponding U.S. Pat. No. 4,571,407 for the treatment of neuropathies, encephalopathies, myelopathies and cerebral edemas.

Besides the compounds mentioned above, *Ginkgo biloba* leaves also contain so-called ginkgolic acids (anacardic acids). These compounds are 6-alkylsalicylic acids with n-$C_{13}$- to n-$C_{19}$-alkyl groups with 0 to 3 double bonds; see J. L. Gellermann et al., Phytochemistry, Vol. 15 (1976), 1959–1961 and Analytic. Chem., Vol. 40 (1968), 739–743.

"Ginkgol", a phenol substituted with the corresponding alkyl group, can be obtained either biogenetically by decarboxylation of the ginkgolic acids or during the technical processing of the *Ginkgo biloba* leaves; see Kawamura, Japan, J. Chem., Vol. 3 (1928), 91–93.

The ginkgolic acids and ginkgols in *Ginkgo biloba* are accompanied by corresponding derivatives with a further phenolic hydroxyl group in 4-position, the 6-alkylresorcin acids or 5-alkylresorcins; see J. Gellermann et al., Phytochemistry, Vol. 15 (1976), 1959–1961. These resorcin derivatives are responsible for the toxic effects and especially for the strong allergies and contact dermatitis caused by toxicodendron plants; see G. A. Hill et al., J. Am. Chem. Soc., Vol. 56 (1934), 2736–2738.

Cases of strong allergic reactions after contact with Ginkgo fruits are known; see W. F. Sowers et al., Arch. Dermatol., Vol. 91 (1965), 452–456, and T. Nakamura, Contact Dermatitis, Vol. 12 (1985), 281–282. Serious mucosal disturbances after eating Ginkgo fruits have been described; see L. E. Becker and G. B. Skipworth, J. Am. Med. Assoc., Vol. 231 (1975), 1162–1163. Allergic skin reactions also occur occasionally on collecting or handling Ginkgo leaves.

The significance of allergies caused by alkylphenol compounds from anacardiaceae and ginkgoaceae is evident from the development of substances and methods of desensitisation described in patent literature (see U.S. Pat. No. 4,428,965) against the allergies caused by alkylphenol compounds.

Commercial extracts from *Ginkgo biloba* leaves contain between 50 and 10,000 ppm ginkgolic acids.

The extracts from *Ginkgo biloba* leaves prepared by the known methods in DE-B 17 67 098 and DE-B 21 17 429 are substantially free of alkylphenol compounds because the lipophilic components of the extract are removed by a liquid-liquid-extraction of the aqueous acetone extract with a substantially water-immiscible lipophilic solvent, e.g. with a chlorinated aliphatic lower hydrocarbon such as carbon tetrachloride. However, in this step, the therapeutically valuable ginkgolides and the bilobalide are also considerably reduced so that their content in the final product in Example 1 of DE-B 21 17 429 is a maximum of 0.5% in the case of ginkgolides A, B, C and J in total and approximately 0.3% in the case of bilobalide. The quantity of flavone glycosides, however, is greatly increased during this step, namely from 3 to 4% in the crude extract to approximately 24% in the final product.

As experiments will demonstrate, flavone glycosides have the property of trapping radicals; see J. Pincemail and C. Deby, La Presse Medicale Vol. 15 (1986), 1475–1479. This effect can be used therapeutically for the stabilization of sensitive cell membranes against attacks from radicals in the cases of pathogenesis of inflammatory and ischemic illnesses. In addition, the flavone glycosides increase peripheral circulation.

The Ginkgo extract used most frequently at present for therapeutic purposes (tanakan[R]; roekan[R] or tebonin[R]; "EGb 761") contains besides 24% flavone glycoside compounds 6% terpene lactone compounds; see K. Drieu, La Presse Medicale Vol. 15 (1986), 1455–1457. These are the ginkgolides A, B, C and J as well as the bilobalide, which makes up approximately half of the 6%. The therapeutic daily dosage is 120 mg.

It is an object of the present invention, with respect to its principal use on elderly people, to reduce the daily dosage of the extract and, in so doing, reduce the size of the pharmaceuticals.

A further object is to enrich the active components of the extract to a content of more than 50% so that the authorities' requirements for pharmaceuticals with regard to analytical definition and reproducible composition, independent from the variable composition of the starting material Ginkgo leaves, can be fulfilled. The highly enriched active component concentrate is also authorized as a pharmaceutical in those countries with high standards for pharmaceutical quality norms which are not usually met by simple extracts since the norms generally apply to pure substances. Until now it has not been possible to prepare such highly concentrated extracts from the leaves of *Ginkgo biloba*.

The extensive removal of inactive accompanying substances also enhances the safety of the pharmaceutical, since the simpler composition of the active component concentrate facilitates a more precise analytical determination of the main components and the detection of potential impurities.

Finally, it is an object of the present invention to provide for a specific therapy the possibility of combining either the ginkgolide components or the bilobalide with the flavone glycosides, that is, on the one hand, shifting the active profile of the extract towards the anti-PAF-effects, or, on the other hand, applying the active profile more effectively against demyelinating neuropathies and cerebral edemas.

It is also an object of the present invention therefore to provide pharmaceuticals which exploit the possibility of specifically combining ginkgolides or bilobalide with the flavone glycosides where there is substantially no danger of allergic reactions precisely because of the removal of the alkylphenol compounds.

The invention therefore relates to a *Ginkgo biloba* extract from the leaves of *Ginkgo biloba* with a content of 40 to 60%, preferably 45 to 55%, flavone glycosides, 5.5–8.0%, in particular 7.0%, ginkgolides A, B, C and J, 5.0–7.0%, preferably 6.0%, bilobalide, from about 0% to less than 10% proanthocyanidins and a maximum of approximately 10 ppm, preferably less than 1 ppm, alkylphenol compounds.

The invention also relates to an extract from the leaves of *Ginkgo biloba* with a content of 40–60%, preferably 45 to 55%, flavone glycosides, 5.5–8,0%, preferably 7.0%, ginkgolides A, B, C and J, less than 0.5%, preferably less than 0.1%, bilobalide, from about 0% to less than 10% proanthocyanidins and a maximum of approximately 10 ppm, preferably less than 1 ppm, alkylphenol compounds.

The invention also relates to an extract from the leaves of *Ginkgo biloba* with a content of 40–60%, preferably 45 to 55%, flavone glycosides, a maximum of 0.1% ginkgolides, 5.0–7.0%, preferably 6.0%, bilobalide, from about 0% to less than 10% proanthocyanidins and a maximum of approximately 10 ppm, preferably less than 1 ppm, alkylphenol compounds.

In addition, the invention relates to a method of preparation of these extracts from *Ginkgo biloba* leaves which comprises the steps described in claims 4–7.

In particular, an embodiment of the invention concerns a method for the preparation of a flavone concentrate from *Ginkgo biloba* leaves with a content of 40–60%, preferably 45–55% flavone glycosides This method is characterized in that fresh or dried green leaves from *Ginkgo biloba* with a high content of flavone glycosides are extracted at a temperature of 40° to 100° C. with either aqueous acetone, an aqueous alkanol having up to 3 c-atoms, or anhydrous methanol. Most of the organic solvent is then separated from the extract to a maximum content of 10%, preferably a maximum content of 5%. The resulting concentrated aqueous solution is then diluted with water to a solids content of 15–20%, and left to cool, while being stirred, to a temperature below 25° C., preferably 10° to 12° C. until a precipitate forms. This precipitate, consisting of the lipophilic components which do not dissolve well in water, is removed. The remaining aqueous solution is then subjected to a multistep extraction with an ester of formic acid or acetic acid having a boiling point below 120° C. This ester is preferably ethyl acetate, or a mixture of ethyl acetate with an aliphatic or cycloaliphatic hydrocarbon having a boiling point of approximately 60°–100° C. in a ratio of 9:1 to 7:3. The dissolved ester (or ester mixture) is removed from the remaining aqueous solution by distillation, and the resultant solution is extracted with a water-immiscible C-4 or C-5 alkanol. The butanol or pentanol phases are then washed with several quantities of water. The alkanol phases are subsequently concentrated and the residual quantities of the solvent are completely removed by azeotropic distillation by adding ethanol and water.

According to another embodiment, the extract obtained with the ethyl acetate or the ethyl acetate/hydrocarbon mixture in the above process is treated with activated carbon to remove accompanying substances. Or the accompanying substances are removed by column chromatography through silica gel or a gel suitable for the separation of substances with a molecular weight of less than 1000, such as sephadex LH-20$^R$.

According to another embodiment, the extract obtained with the ester or the ester/hydrocarbon mixture above is first treated with activated carbon to remove accompanying substances. Thereafter, the ginkgolides are crystallized. Pure bilobalide and remaining ginkgolides are then separated from the mother liquor by column chromatography.

According to yet another embodiment, after suspending the above flavone concentrate in a water/alcohol mixture, the resulting solution is extracted with an aliphatic or cycloaliphatic solvent with a boiling point of approximately 60°–100° C., in order to reduce the alkylphenol compounds to a content of 10 ppm, preferably 1 ppm. The water phase is then concentrated under reduced pressure and evaporated at a temperature of 60°–80° C. to a dry extract with a water content of less than 5%.

In contrast to the method of preparation described in DE-B 17 67 098, the aqueous alcohol or aqueous acetone crude extract prepared from Ginkgo leaves with a content of at least 1.4% flavone glycosides is not directly subjected to a liquid-liquid-extraction with a chlorinated aliphatic hydrocarbon, but rather most of the lipophilic components which precipitate on removal of the organic solvent component by distillation to a maximum content of approximately 10%, preferably a maximum of 5% (whereby water can be added in the last distillation steps, especially if methanol is used), are separated by filtration. The alkylphenol compounds, the chlorophyll, the fatty acid derivatives and the biflavones precipitate due to their poor solubility in water and can be separated by filtration. Under these conditions, the desired components of the *Ginkgo biloba* extract remain dissolved. The ginkgolides and the bilobalide are subsequently separated from the aqueous extract solution by a multistep liquid-liquid extraction with an ester of formic acid or acetic acid with a boiling point of below 120° C., whereby up to 30 percent by volume aliphatic or cycloaliphatic hydrocarbon with a boiling point of 60° to 100° C. can be added. The organic phases are treated with activated carbon to remove accompanying substances and the ginkgolides are recrystallized from the solutions which are concentrated to dryness by dissolving in ethanol/water or methanol/water. Pure bilobalide and further quantities of ginkgolides are obtained from the mother liquor by column chromatographic separation.

For the preparation of an extract containing both ginkgolides and bilobalide, the separation of these compounds from one another is not necessary. A ginkgolide/bilobalide concentrate is prepared by removing accompanying substances by column chromatography with gels suitable for the separation of molecules with a molecular weight of below 1000.

A flavone concentrate with at least 40% flavone glycosides is prepared out of the water phase by a multistep liquid-liquid-extraction with an alkanol of 4 C-atoms which is not completely miscible with water, that is, all isomeric butanols with the exception of tert-butanol, or with an alkanol of 5 C-atoms which is not completely miscible with water, that is, all isomeric amyl alcohols or pentanols. To remove the compounds which dissolve well in water, the alkanol phases can be washed several times in small quantities of water, this having the effect of enriching the flavone compounds.

The alkylphenol compounds are reduced further to a content of less than 10 ppm in a subsequent defatting step by subjecting an aqueous ethanol solution of the extract fractions recombined according to the corresponding desired final product, e.g. flavone glycosides and ginkgolides or flavone glycosides and bilobalide, to a multistep liquid-liquid-extraction with an aliphatic hydrocarbon with a boiling point of 60° to 100° C. The water phase is concentrated under reduced pressure and evaporated at a temperature of 60°–80° C. to a dry extract with a water content of less than 5%.

In addition, the present invention relates to pharmaceuticals which according to claim 8 are characterized by a content of *Ginkgo biloba* extract.

The Ginkgo extracts can be processed in the usual way for the preparation of pharmaceuticals, e.g. to solutions, coated tablets, tablets or injection preparations. The pharmaceuticals in Example 3 of the invention are used for the treatment of peripheral and cerebral arterial circulatory disturbances.

The active component concentrate in Example 4 is used mainly for the treatment of illnesses in which the platelet activating factor (PAF) plays a pathogenetic role.

The active component concentrate in Example 5 is used mainly against demyelinating neuropathies and cerebral edemas.

Examples 1–7 illustrate the invention.

EXAMPLE 1

640 kg of dry *Ginkgo biloba* leaves with a flavone glycoside content of 1.5% are crushed in a mill to a particle size of 1.5–4 mm. This is then percolated in 12 steps with 2600 kg of 60 weight percent aqueous acetone at a temperature of 57° to 59° C. The aqueous acetone extract is filtered and concentrated under reduced pressure to a solids content of approximately 30% and a maximum of approximately 5 weight percent acetone. The concentrate is diluted with water to double its volume and left to cool, while being stirred, to approximately 12° C. After one hour at this temperature the resultant precipitate is separated by centrifugation and the solution is passed through a filter until clear.

The filtrate is extracted three times, each time with ⅓ of its volume of ethyl acetate/n-hexane in ratio 9:1. The organic phases are washed twice, each time with 20% of their volume of water, four times their weight of active carbon is added, based on their solids content, and this is stirred for one hour. The activated carbon is separated by filtration and washed with a small quantity of ethyl acetate. The filtrate and the wash solution are evaporated under reduced pressure. The residue is dissolved in four times its weight of 50 weight percent ethanol/water at boiling temperature. When the solution has cooled, the ginkgolides crystallize as a mixture: quantity 410 g. After separation of the crystals, the mother liquor is evaporated under reduced pressure and separated by column chromatography with ten times its weight of silica gel in the solvent toluene/acetone 88:12 parts by volume. The separation is monitored by thin-layer chromatography. All of the fractions containing bilobalide are collected separately, combined and reduced to dryness: 595 g. The fractions containing ginkgolides are likewise combined and reduced to dryness: 650 g.

The water phase from the liquid-liquid-extraction with ethyl acetate/n-hexane is freed from the dissolved ethyl acetate/n-hexane under reduced pressure and extracted three times with ⅓ of its volume of n-butanol. The combined butanol phases are washed three times, each time with 20% of their volume of water. The butanol is separated by distillation under reduced pressure and, after adding ethanol/water, completely removed by distillation. The resultant solid matter (11.2 kg) represents the ginkgo flavone concentrate with a content of approximately 54% flavone glycosides. From this ginkgo flavone concentrate, a solution is prepared in 40 weight percent ethanol/water with 5% solids content.

EXAMPLE 2

20 kg of dried *Ginkgo biloba* leaves with a flavone glycoside content of 1.6% are extracted twice, each time with 140 kg of 60 weight percent acetone for one hour at reflux temperature. The extracts from both extraction steps are filtered and concentrated under reduced pressure to a solids content of approximately 30%. The concentrate is diluted with water to approximately 15% and left to cool, while being stirred, to approximately 12° C. The resultant solution is decanted from the precipitate and filtered until clear.

The filtrate is extracted three times with ⅓ of its volume of ethyl acetate. The organic phases are washed twice, each time with 20% of their volume of water and dried under reduced pressure: 132 g residue.

The substance is dissolved in 400 ml of 52 weight percent ethanol and poured into a column filled with 1000 g of a hydroxypropylated dextran gel (sephadex LH-20$^R$). An elution is carried out with 52 weight percent ethanol and fractions of 80 ml are collected separately. The separation is monitored by thin-layer chromatography. All the fractions containing ginkgolides and bilobalide without accompanying substances are combined. The solvent is separated by distillation under reduced pressure and the precipitating substances are dissolved by adding 1 liter of 95 weight percent ethanol.

The solids content and the content of ginkgolides and bilobalide are determined.

The water phase from the liquid-liquid-extraction with ethyl acetate is freed under reduced pressure from the dissolved ethyl acetate and extracted three times, each time with ⅓ of its volume of butan-2-ol. The combined organic phases are washed three times, each time with 20% of their volume of water. The butan-2-ol is distilled off under reduced pressure and, on adding a small quantity of ethanol and water, completely removed by distillation. The residue (320 g flavone concentrate) is dissolved in 4 kg of 40 weight percent aqueous ethanol.

EXAMPLE 3

Extract with 50% ginkgo flavone glycosides, 7% ginkgolides A, B, C and J and 6% bilobalide.

The solution of 320 g flavone concentrate in 4 kg of 40 weight percent aqueous ethanol according to Example 2 is mixed with the analytically determined quantity of ginkgolide-bilobalide solution according to Example 2 containing approximately 26 g ginkgolides and 22 g bilobalide. The entire solution is extracted five times, each time with 2 liters of n-heptane. The water phase is concentrated under reduced pressure and the dry extract is dried in vacuum at 60° C., crushed through a sieve and mixed until homogeneous. Yield: 359 g.

EXAMPLE 4

Extract with 50% ginkgo flavone glycosides and 7% ginkgolides A, B, C and J.

200 kg solution of the flavone concentrate according to Example 1 are mixed with a solution containing 750 g ginkgolides A, B, C and J (obtained according to Example 1) in 50 kg of 95 weight percent ethanol. The mixture is stirred five times with 80 liters of n-heptane. The water phase is concentrated under reduced pressure and then evaporated in vacuum by microwave radiation. Yield: 10.3 kg.

EXAMPLE 5

Extract with 50% ginkgo flavone glycosides and 6% bilobalide.

1.88 kg solution of the flavone concentrate according to Example 1 is mixed with a solution of 6 g bilobalide (free of ginkgolides, obtained according to Example 1) in approximately 500 ml of 95 weight percent ethanol and this solution is extracted five times with ⅓ of its volume of cyclohexane. The water phase is concentrated under reduced pressure to dryness. The dry extract is dried again in vacuum at 60° C., crushed through a sieve and mixed until homogeneous. Yield: 98.3 g.

EXAMPLE 6

Solution for oral administration:
100 ml solution contains:

| | |
|---|---|
| Ginkgo biloba active component concentrate as in Examples 3–5 | 2.0 g |
| ethanol | 50.0 g |
| demineralised water to | 100.0 ml |

EXAMPLE 7

Coated tablets:

| 1 tablet contains: | |
|---|---|
| Ginkgo biloba active component concentrate in Examples 3–5 | 20.00 mg |
| microcrystalline cellulose | 50.00 mg |
| lactose | 40.00 mg |
| colloidal silicic acid | 12.50 mg |
| talcum | 2.25 mg |
| magnesium stearate | 0.25 mg |
| hydroxypropyl methylcellulose | 8.00 mg |
| ferric oxide pigment | 0.05 mg |
| talcum | 0.25 mg |
| weight of a coated tablet | approx. 133.36 mg |

We claim:

1. An extract from the leaves of *Ginkgo biloba* comprising 40–60% flavone glycosides, 5.5–8.0% ginkgolides selected from ginkgolides A, B, C and J or mixtures thereof, 0.5–7.0% bilobalide, from about 0% to less than 10% proanthocyanidins and a maximum of approximately 10 ppm alkylphenol compounds.

2. An extract from the leaves of *Ginkgo biloba* comprising 40–60% flavone glycosides, 5.5–8.0% ginkgolides selected from ginkgolides A, B, C and J or mixtures thereof, less than 0.5% bilobalide, from about 0% to less than 10% proanthocyanidins and a maximum of approximately 10 ppm alkylphenol compounds.

3. An extract from the leaves of *Ginkgo biloba* comprising 40–60% flavone glycosides, a maximum of 0.1% ginkgolides, 5.0–7.0% bilobalide, from about 0% to less than 10% proanthocyanidins and a maximum of approximately 10 ppm alkylphenol compounds.

4. A method for preparation of a flavone concentrate from *Ginkgo biloba* leaves with a content of 40–60% flavone glycosides wherein:
   a) fresh or dried green leaves from *Ginkgo biloba* with at least 1.4% flavone glycosides are extracted at a temperature of 40° to 100° C. with an organic solvent selected from the group consisting of aqueous acetone, an aqueous alkanol with up to 3 C-atoms and anhydrous methanol,
   b) the organic solvent is separated from the extract to a maximum content of 10% to form a concentrated aqueous solution,
   c) the concentrated aqueous solution is diluted with water to a solids content of 15–20% by weight, and left to cool, while being stirred, to a temperature below 25° C., until a precipitate forms and this precipitate, consisting of the lipophilic components which to not dissolve well in water, is filtered off,
   d) the remaining aqueous solution from step (c) is subjected to a multistep extraction with an ester of formic acid or acetic acid with a boiling point below 120° C. to form an extract,
   e) the ester from step (d) and remaining solvent is removed from the remaining aqueous solution by distillation,
   f) the resultant solution is extracted with a water-immiscible C-4 or C-5 alkanol at ambient temperature,
   g) the alkanol phases are washed with water,
   h) the alkanol phases are subsequently concentrated and the residual quantities of the solvent are completely removed by azeotropic distillation, and
   i) the residue from step (h) is diluted with 40 weight percent ethanol and water to form a diluted residue.

5. The method of claim 4 wherein step (d) further comprises treating the extract with activated carbon to remove accompanying substances.

6. The method of claim 4 wherein step (d) further comprises treating the extract with activated carbon to remove accompanying substances, then the ginkgolides from the treated extract are recrystallized and pure bilobalide and additional ginkgolides are separated from the treated extract by column chromatography.

7. The method of claim 4, 5 or 6, wherein the diluted residue of claim 4(i) is further extracted with an aliphatic or cycloaliphatic solvent with a boiling point of approximately 60° to 100° C., and the water phase is concentrated under reduced pressure and evaporated at a temperature of 60°–80° C. to a dry extract with a water content of less than 5%.

8. The extract of claim 1, 2 or 3 containing about 45 to 55% flavone glycosides.

9. The extract of claim 1 or 2 containing about 7% by weight ginkgolides A, B, C and J.

10. The extract of claim 1 or 3 containing about 6% by weight bilobalide.

11. The extract of claim 2 containing less than 0.1% by weight bilobalide.

12. The extract of claim 1, 2, or 3 containing less than 1 ppm alkylphenol compounds.

13. The method of claim 4 wherein the flavone concentrate contains about 45 to 55% flavone glycosides.

14. The method of claim 4 wherein the organic solvent in step (b) is separated from the extract to a maximum content of 5%.

15. The method of claim 4 wherein the concentrated aqueous solution of step (c) is cooled to a temperature of approximately 10° to 12° C.

16. The method of claim 4 wherein the ester of step (d) is ethyl acetate.

17. The method of claim 4 wherein the extraction in step (d) is conducted with a mixture of ethyl acetate and an aliphatic hydrocarbon with a boiling point of approximately 60° to 100° C. in a ratio of 9:1 to 7:3.

18. The method of claim 4 wherein the alkanol of step (f) is n-butanol.

19. The method of claim 4 wherein the extract obtained from step (d) is further treated to remove accompanying substances by column chromatography through a silica gel or a gel suitable for the separation of substances having a molecular weight of less than 1000.

20. The method of claim 19 wherein the gel having a molecular weight of less than 1000 is hydroxy propylated dextran gel.

* * * * *

UNITED STATES PATENT AND TRADEMARK OFFICE
CERTIFICATE OF CORRECTION

PATENT NO. : 5,389,370
DATED : February 14, 1995
INVENTOR(S) : Joseph O'REILLY et al.

It is certified that error appears in the above-indentified patent and that said Letters Patent is hereby corrected as shown below:

Column 8, line 12, change "approx. 133.36 mg" to --approx. 133.30 mg--.

Signed and Sealed this

Twenty-third Day of May, 1995

Attest:

BRUCE LEHMAN

*Attesting Officer*  *Commissioner of Patents and Trademarks*